(12) United States Patent
Blease et al.

(10) Patent No.: US 10,379,072 B2
(45) Date of Patent: Aug. 13, 2019

(54) MULTIPLE DETECTOR APPARATUS AND METHOD FOR MONITORING AN ENVIRONMENT

(71) Applicant: R.R. DONNELLEY & SONS COMPANY, Chicago, IL (US)

(72) Inventors: James W. Blease, Avon, NY (US); Theodore F. Cyman, Jr., Grand Island, NY (US); Alan R. Murzynowski, Grand Island, NY (US); Kevin J. Hook, Grand Island, NY (US)

(73) Assignee: Cryovac, LLC, Charlotte, NC (US)

( * ) Notice: Subject to any disclaimer, the term of this patent is extended or adjusted under 35 U.S.C. 154(b) by 0 days.

(21) Appl. No.: 15/398,510

(22) Filed: Jan. 4, 2017

(65) Prior Publication Data

US 2017/0191952 A1 Jul. 6, 2017

Related U.S. Application Data

(60) Provisional application No. 62/274,593, filed on Jan. 4, 2016.

(51) Int. Cl.
*G01N 7/00* (2006.01)
*G01N 21/00* (2006.01)
(Continued)

(52) U.S. Cl.
CPC ............. *G01N 27/125* (2013.01); *B01L 3/50* (2013.01); *G01N 27/126* (2013.01);
(Continued)

(58) Field of Classification Search
CPC .......... G01N 7/00; G01N 21/00; G01N 27/00; G01N 31/00; G01N 33/00
(Continued)

(56) References Cited

U.S. PATENT DOCUMENTS

| 3,559,619 A | 2/1971 | Johnson |
| 4,012,552 A | 3/1977 | Watts |

(Continued)

FOREIGN PATENT DOCUMENTS

| EP | 1019715 | 1/2005 |
| FR | 2 997 218 A1 | 4/2014 |

(Continued)

OTHER PUBLICATIONS

International Search Report and Written Opinion dated Aug. 23, 2018, for International Application No. PCT/US2018/035403, Applicant, R.R. Donnelley & Sons Company (15 pages).

(Continued)

*Primary Examiner* — Brian J. Sines
(74) *Attorney, Agent, or Firm* — McCracken & Gillen LLC

(57) ABSTRACT

According to one aspect, a monitoring device for detecting when an object may be subjected to a condition includes a processor, a first sensor, a second sensor, and a configuration circuit. A first sensor is polymer monolayer adapted to detect if the object is subjected to a magnitude of a first condition. A second sensor is a polymer bilayer adapted to detect if the object is subjected to a magnitude of a second condition. The resistance across the first sensor and second sensor are compared to determine whether an ambient/environmental condition has been detected. Indication of detection of an ambient/environmental condition, magnitude of the condition, and the time may be stored.

19 Claims, 5 Drawing Sheets

(51) Int. Cl.
    *G01N 27/00*     (2006.01)
    *G01N 31/00*     (2006.01)
    *G01N 33/00*     (2006.01)
    *G01N 27/12*     (2006.01)
    *B01L 3/00*     (2006.01)

(52) U.S. Cl.
    CPC ..... *G01N 33/0031* (2013.01); *G01N 33/0063* (2013.01); *B01L 2300/023* (2013.01); *B01L 2300/027* (2013.01); *B01L 2300/0663* (2013.01); *B01L 2300/0816* (2013.01)

(58) Field of Classification Search
    USPC ..... 422/50, 68.1, 83, 84, 88, 90, 98; 436/43, 436/149
    See application file for complete search history.

(56) References Cited

U.S. PATENT DOCUMENTS

| | | | |
|---|---|---|---|
| 4,368,281 A | 1/1983 | Brummett et al. | |
| 4,515,653 A * | 5/1985 | Furubayashi | G01N 27/126 204/192.32 |
| 4,632,879 A | 12/1986 | Tanaka et al. | |
| 5,232,532 A | 8/1993 | Hori | |
| 5,482,553 A | 1/1996 | Loftin et al. | |
| 5,520,763 A | 5/1996 | Johnstone | |
| 5,581,065 A | 12/1996 | Nishikawa et al. | |
| 5,790,020 A | 8/1998 | Sasagawa et al. | |
| 5,802,015 A | 9/1998 | Rothschild et al. | |
| 6,019,865 A | 2/2000 | Palmer et al. | |
| 6,043,745 A | 3/2000 | Lake | |
| 6,223,799 B1 | 5/2001 | Johnstone | |
| 6,420,096 B1 | 7/2002 | Löbl et al. | |
| 6,421,013 B1 | 7/2002 | Chung | |
| 6,544,864 B2 | 4/2003 | Reeder et al. | |
| 6,853,087 B2 | 2/2005 | Neuhaus et al. | |
| 6,886,745 B2 | 5/2005 | Berrube et al. | |
| 6,888,509 B2 | 5/2005 | Atherton | |
| 6,924,781 B1 | 8/2005 | Gelbman | |
| 7,042,357 B2 | 5/2006 | Girvin et al. | |
| 7,057,495 B2 | 6/2006 | Debord et al. | |
| 7,168,626 B2 | 1/2007 | Lerch et al. | |
| 7,174,277 B2 | 2/2007 | Vock et al. | |
| 7,204,425 B2 | 4/2007 | Mosher, Jr. et al. | |
| 7,248,147 B2 | 7/2007 | Debord et al. | |
| 7,283,054 B2 | 10/2007 | Girvin et al. | |
| 7,295,115 B2 | 11/2007 | Aljadeff et al. | |
| 7,316,358 B2 | 1/2008 | Kotik et al. | |
| 7,323,360 B2 | 1/2008 | Gonzalez et al. | |
| 7,377,447 B2 | 5/2008 | Oberle | |
| 7,417,541 B2 | 8/2008 | Lerch et al. | |
| 7,586,412 B2 | 9/2009 | Takatama | |
| 7,627,451 B2 | 12/2009 | Vock et al. | |
| 7,639,135 B2 | 12/2009 | Arms et al. | |
| 7,737,839 B1 | 6/2010 | Jones | |
| 7,802,222 B2 | 9/2010 | Arsintescu | |
| 7,856,339 B2 | 12/2010 | Vock et al. | |
| 7,895,739 B2 | 3/2011 | Niklas et al. | |
| 7,945,320 B2 | 5/2011 | Durand | |
| 7,993,055 B2 | 8/2011 | Nurse et al. | |
| 8,126,675 B2 | 2/2012 | Vock et al. | |
| 8,203,446 B2 | 6/2012 | Tsubota et al. | |
| 8,219,466 B2 | 7/2012 | Gui et al. | |
| 8,280,682 B2 | 10/2012 | Vock et al. | |
| 8,317,084 B2 | 11/2012 | Bagai | |
| 8,334,226 B2 | 12/2012 | Nhan et al. | |
| 8,354,927 B2 | 1/2013 | Breed | |
| 8,428,904 B2 | 4/2013 | Vock et al. | |
| 8,590,799 B2 | 11/2013 | Liu | |
| 8,618,914 B2 | 12/2013 | Bachman et al. | |
| 8,640,259 B2 | 1/2014 | Jung et al. | |
| 8,747,775 B2 | 6/2014 | Sandvick | |
| 8,762,212 B2 | 6/2014 | Falls et al. | |
| 8,870,083 B2 | 10/2014 | Myers et al. | |
| 9,030,724 B2 | 5/2015 | Agrawal et al. | |
| 9,047,437 B2 | 6/2015 | Chen et al. | |
| 9,077,183 B2 | 7/2015 | Thomas et al. | |
| 9,087,318 B1 | 7/2015 | Cordes et al. | |
| 9,495,498 B2 | 11/2016 | Bartley et al. | |
| 9,514,432 B2 | 12/2016 | Cyman, Jr. et al. | |
| 10,089,594 B2 | 10/2018 | Gray | |
| 2002/0028599 A1 | 3/2002 | Reeder et al. | |
| 2003/0080437 A1 | 5/2003 | Gonzalez et al. | |
| 2004/0066296 A1 | 4/2004 | Atherton | |
| 2006/0043584 A1 | 3/2006 | Niklas et al. | |
| 2006/0103534 A1 | 5/2006 | Arms et al. | |
| 2006/0254440 A1 | 11/2006 | Choi et al. | |
| 2008/0154101 A1* | 6/2008 | Jain | A61B 5/0017 600/309 |
| 2010/0176950 A1 | 7/2010 | Bartholf et al. | |
| 2011/0131854 A1 | 6/2011 | Waltersdorf | |
| 2012/0038461 A1 | 2/2012 | Forster | |
| 2012/0071742 A1 | 3/2012 | Medina et al. | |
| 2012/0162945 A1 | 6/2012 | Schreiner | |
| 2013/0317659 A1 | 11/2013 | Thomas et al. | |
| 2014/0196847 A1 | 7/2014 | Bergherm | |
| 2015/0079697 A1 | 3/2015 | Belbruno et al. | |
| 2016/0050762 A1 | 2/2016 | Cyman, Jr. et al. | |
| 2016/0148899 A1 | 5/2016 | Ichimura | |
| 2016/0249840 A1* | 9/2016 | Pesantez | A61B 5/14865 205/778 |
| 2017/0053235 A1 | 2/2017 | Cyman, Jr. et al. | |
| 2017/0076642 A1 | 3/2017 | Cyman, Jr. et al. | |
| 2017/0138922 A1* | 5/2017 | Potyrailo | G01N 33/2888 |
| 2017/0191953 A1* | 7/2017 | Rigas | G01N 27/126 |
| 2017/0229000 A1 | 8/2017 | Law | |
| 2017/0354372 A1* | 12/2017 | Varadan | A61B 5/04085 |

FOREIGN PATENT DOCUMENTS

| | | |
|---|---|---|
| JP | 2003-277653 | 10/2003 |
| JP | 2011-151259 | 8/2011 |
| WO | WO 00/73082 | 12/2000 |
| WO | WO 03/06736 | 1/2003 |
| WO | WO 14/67578 | 5/2014 |
| WO | WO 2015/004830 | 1/2015 |
| WO | WO 2015/160830 | 10/2015 |

OTHER PUBLICATIONS

U.S. Appl. No. 15/451,036, R.R. Donnelley & Sons Company.
Non-Final Office action dated Jun. 8, 2017, for U.S. Appl. No. 14/825,986, Applicant, R.R. Donnelley & Sons Company (9 pages).
Final Office action dated Oct. 25, 2017, for U.S. Appl. No. 14/825,986, Applicant, R.R. Donnelley & Sons Company (7 pages).
U.S. Appl. No. 14/996,413, R.R. Donnelley & Sons Company.
U.S. Appl. No. 15/043,885, R.R. Donnelley & Sons Company.
Non-Final Office Action dated Dec. 2, 2016, for U.S. Appl. No. 15/043,885, Applicant, R.R. Donnelley & Sons Company (8 pages).
International Search Report and Written Opinion dated Nov. 25, 2015, for International Application No. PCT/US2015/045922, Applicant R.R. Donnelley & Sons Company (11 pages).
Non-final Office action dated Oct. 12, 2016, for U.S. Appl. No. 14/853,563, Applicant, R.R. Donnelley & Sons Company (9 pages).
International Search Report and Written Opinion dated Oct. 8, 2015, for International Application No. PCT/US2015/045089, Applicant, R.R. Donnelley & Sons Company (10 pages).
International Search Report and Written Opinion dated Oct. 20, 2015, for International Application No. PCT/US2015/045128, Applicant, R.R. Donnelley & Sons Company (10 pages).
International Search Report and Written Opinion dated Apr. 6, 2017, for International Application No. PCT/US2017/013464, Applicant, R.R. Donnelley & Sons Company (14 pages).
Duck, A., Dispensing SMD Adhesives: Rotary Pump Technology vs. Stencil Printing Technology, Electronic Packaging and Production, Aug. 1, 1996, pp. 41-44, vol. 36, No. 9, Cahners Publishing Co, Newton Massachusetts, U.S. (4 pages).

(56) References Cited

OTHER PUBLICATIONS

International Search Report and Written Opinion dated Apr. 12, 2017, for International Application No. PCT/US2017/012178, Applicant, R.R. Donnelley & Sons Company (18 pages).

* cited by examiner

MULTIPLE DETECTOR APPARATUS AND METHOD FOR MONITORING AN ENVIRONMENT

CROSS REFERENCE TO RELATED APPLICATIONS

The present application claims the benefit of U.S. Provisional Patent Application No. 62/274,593, filed Jan. 4, 2016, entitled "Multiple Detector Apparatus and Method for Monitoring an Environment", owned by the assignee of the present application and the disclosure of which is incorporated by reference herein.

FIELD OF THE DISCLOSURE

The present subject matter relates to environmental sensing, and more particularly to an apparatus and method for monitoring an environment.

BACKGROUND OF THE DISCLOSURE

During use or otherwise, an object may be exposed to one or more ambient environmental conditions that may damage or otherwise adversely affect the object. A party, such as an owner or other having an interest in the object, may wish to determine whether the object was so exposed. For example, a lessor of a rental automobile may wish to determine upon return of the automobile to the lessor whether the vehicle interior was exposed to tobacco smoke.

Knowledge of exposure to other conditions such as extreme temperatures and/or humidity, chemicals, radiation (including visible or invisible light), forces, odors, and the like may be of interest in connection with other articles. For example, fine art, electronic components, and the like may be harmed or damaged if subjected to certain atmospheres. Similarly, foods, liquids, and pharmaceuticals may be harmed if exposed to temperatures and/or humidity outside of predetermined ranges.

Further, exposure of an object and/or damage thereto may not be quantifiable by a routine inspection. Exposure to forces or extremes in temperature or other ambient condition may not cause visually perceptible changes, but may affect the operating characteristics, effectiveness, longevity, and/or value (perceived or real) of the good. For example, the detection of an objectionable odor may be subjective, but the presence of such an odor can decrease the value of a rental car or hotel room. Likewise, the effectiveness of a pharmaceutical may be altered if such pharmaceutical is exposed to extreme temperatures or unsuitable atmospheres. Similarly, harm may occur when a person is subjected to airborne pollutants, as may occur from second-hand smoke or enclosed environments having poor ventilation.

In addition, when a customer reports to an owner that an object was already damaged (e.g., a vehicle or hotel room was smoked in), it may be difficult for the customer and owner to prove when the exposure occurred, and who is accountable for such damage.

In certain monitoring devices, a processor is powered on and becomes active periodically to poll a sensor in the device. Such devices typically require a battery with sufficient capacity to allow the processor to become active many times while the object is being monitored. A battery that has sufficient capacity may be bulky and may add to the cost of the device. Because the processor remains active, heat sinks may also have to be used to draw heat away from the monitoring device and the object. Because of these considerations, such devices may be larger, heavier, and more expensive in order to be used routinely.

SUMMARY

According to one aspect, a monitoring device for detecting the environment to which an object is subjected includes a carrier, a processor, a first sensor comprising a conductive polymer configured to detect when the object is subjected to at least a first magnitude of a first condition, a second sensor comprising a polymer bilayer configured to detect when the object is subjected to a second magnitude of a second condition and a configuration circuit for specifying a first configuration parameter and a second configuration parameter. The configuration parameters include a second magnitude of the first condition, and a second magnitude of the second condition. A comparison is made of the first magnitudes and the second magnitudes and used to determine the level of nicotine exposure the object has encountered.

A monitoring device for detecting a particular condition, comprising: a first carrier; a processor disposed on the first carrier; a first polymer sensor disposed on the first carrier, wherein the first polymer sensor is coupled to the processor and adapted to detect when the monitoring device is subjected to at least a first magnitude of a first condition; a second polymer sensor disposed on the first carrier, wherein the second polymer sensor is coupled to the processor and adapted to detect when the monitoring device is subjected to at least a second magnitude of a second condition; a second carrier disposed over at least a portion of the processor, the first polymer sensor, and the second polymer sensor, wherein the processor generates a signal in response to detection of the first polymer sensor being subjected to at least a first magnitude of the first condition and the second polymer sensor being subjected to less than the second magnitude of the second condition, and the processor provides a determination of a magnitude of the particular condition and generates a second signal if the magnitude of the particular condition is greater than a baseline value.

A monitoring device for detecting a particular condition, comprising: a first carrier; a processor disposed on the first carrier; a first polymer sensor disposed on the first carrier, wherein the first polymer sensor comprises polyaniline and is exhibits an increase in resistance when a first substance is adsorbed on the first polymer sensor; a second polymer sensor disposed on the first carrier, wherein the second polymer sensor comprises polyvinyl alcohol and exhibits an increase in resistance when a second substance is adsorbed on the second polymer sensor; a second carrier disposed over at least a portion of the processor, the first polymer sensor, and the second polymer sensor; and wherein the processor generates a signal in response to detection of the first polymer sensor being subjected to a first magnitude of the first substance and the second polymer sensor being subjected to less than the second magnitude of the second substance, and wherein the processor provides a determination of a magnitude of the particular condition and generates a second signal if the magnitude of the particular condition is greater than a baseline value.

A method of detecting that a device has been subjected to an environmental condition, comprising: providing a device comprising a first polymer sensor, a second polymer sensor and a processor; detecting when the first polymer sensor is subjected to at least a first magnitude of a first condition by measuring resistance across the first polymer sensor; detecting when the second polymer sensor is subjected to less than first magnitude of a second condition by measuring resistance across the second polymer sensor; determining whether the environmental condition has been detected; generating a signal in response to detection of a magnitude of the environmental condition; and generating an indication of a third magnitude of the environmental condition, wherein the third magnitude is greater than or equal to a baseline magnitude.

Other aspects and advantages will become apparent upon consideration of the following detailed description and the attached drawings wherein like numerals designate like structures throughout the specification.

DETAILED DESCRIPTION OF THE EMBODIMENTS

A monitoring device as disclosed herein can determine the ambient environment of an object at least at a particular point in time, and more preferably, over a period of time. The monitoring device includes a processor, memory, at least one and, more preferably, two or more primary ambient sensors, a radio frequency identification (RFID) transceiver and/or other communication device(s) (wired or wireless), and optionally one or more light emitting diodes (LEDs). The device may further include one or more secondary ambient sensors that measure, for example, the presence of airborne pollutants and/or odors, the temperature, and/or the humidity in the ambient environment surrounding the device. Such a device may be affixed to a surface (e.g., the interior surface of a vehicle), and the processor in the device periodically polls the primary ambient sensor(s) and the optional secondary ambient sensors to acquire therefrom measurements associated with one or more ambient condition(s). The processor records in the memory such measurements and a timestamp of when each such measurement was acquired to create a log. The processor may thereafter retrieve the measurement(s) from the memory and optionally process the measurement(s) to derive an indication of whether an ambient threshold or other condition has been detected. Alternatively, the measurements may be supplied to and/or from a memory associated with an external processor separate from the device. The external processor and/or the processor in the device may develop an indication of whether the ambient threshold or other condition has been detected. In either event, data are transferred from the processor by the RFID transceiver or other communication device(s). Preferably, multiple sensors are used to obtain a more specific identification of a particular chemical or class of chemicals, as compared to the identification that can be achieved using a single sensor.

In a specific embodiment, one or more of the sensors comprises a conductive monolayer polymer and at least one other sensor comprising the same conductive polymer and one or more filters in a bilayer or other multilayer arrangement. In the same or another embodiment, one sensor could employ a first conductive polymer and another sensor could employ a second conductive polymer that is different than the first conductive polymer. Either or both of the sensors could include one or more filters.

Figure 1A:
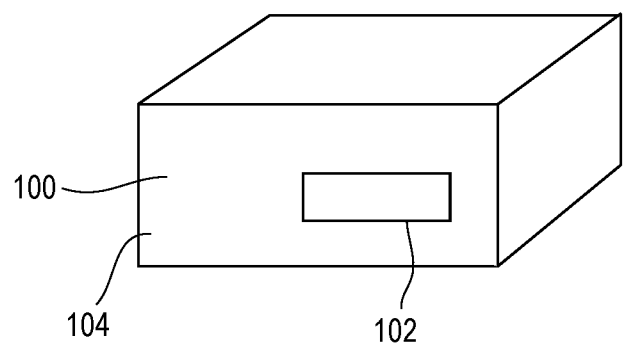
FIG. 1A is an isometric view of a monitoring device affixed to a surface of an object in accordance with the present disclosure.
Figure 1B:
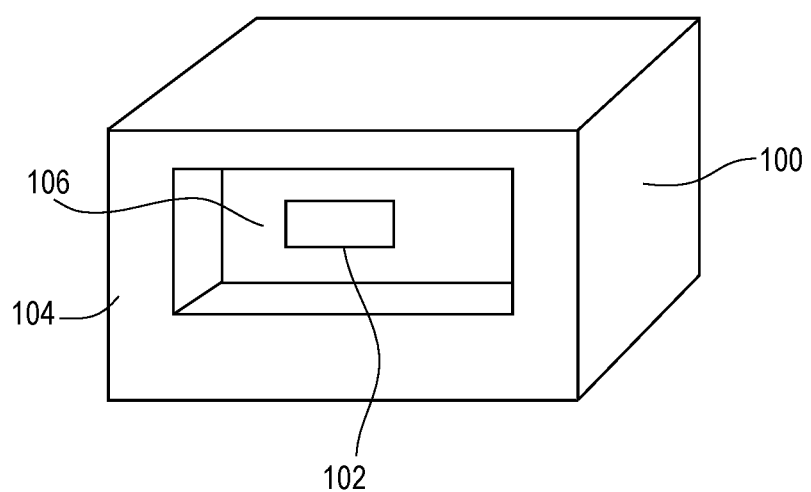
FIG. 1B is an isometric view of a monitoring device affixed to an interior surface of an object in accordance with the present disclosure.

More specifically, referring to FIGS. 1A and 1B, an object 100 has a monitoring device 102 affixed to an outer surface 104, an inner surface 106, or any other portion thereof. It should be noted that the object may be any item(s) (e.g., a vehicle, a package, a room or other environment, a finished or an unfinished good or goods, whether packaged or not, or any other article or articles). As described below, the monitoring device 102 may be configured to store data regarding exposure of the device 102, and therefore the object 100, to one or more ambient influences or a lack of such exposure at one or more points in time in a memory of the device 102 or in another device (whether local or remote from the device 102). The ambient influence(s) may include an environmental condition, a force, disposition of the object 100 in one or more particular orientations, or any other influence that can be detected as noted in greater detail hereinafter. Such stored data may thereafter be retrieved over a wired or wireless connection and analyzed to determine one or more conditions to which the object 100 was exposed. The data may indicate where, when, and/or how the object 100 was subjected to the one or more condition(s) and/or who and/or what caused such condition(s) to occur. For example, such condition(s) may arise from mishandling of a vehicle, for example, by a rental customer during a time period when the vehicle was in possession of the rental customer.

Specific embodiments comprehend the use of analog and/or digital sensors, together with any associated necessary or desirable conditioning and/or interface circuits that are used together with a processor to develop one or more indications of package condition(s) (possibly, dependent upon package contents) at one or more points in time, such as, but not limited to, exposure to smoke and/or other gas(es) or material(s) (including particulates and/or other solids, or liquids) (including biological agent(s), odorants, package handling, orientation, package and/or ambient temperature, position, movement, vibration, acceleration, placement in a vehicle or other device, pressure and/or humidity, exposure to nuclear and/or electromagnetic radiation (including visible and invisible light, x-rays, alpha, beta, or gamma rays), exposure to magnetic fields, first and higher degrees of rate of change of any one or more parameters or conditions, first and higher degrees of integration of one or more parameters or conditions, and/or the like, and combinations thereof. The monitoring device 102 may also include a timer (which may be a stand-alone device or implemented by the processor), and/or sensors that indicate that the monitoring device 102 has been tampered with and/or otherwise altered.

In general, one or more of any condition(s) may be sensed and the processor may develop, for example, an indication of whether a threshold for each such condition, or combinations of conditions, was reached or exceeded, and/or a histogram of each such parameter could be developed. Any such threshold(s) are dependent the condition(s) that are sensed. Such indication(s) and/or the raw data developed by the sensor(s) may be stored locally in a memory associated with the processor of the device 102, and/or such indication(s) may be transmitted to a remote location by any suitable transmission modality, as desired, for analysis, display, and/or any other purpose. Such transmission modalities may include RFID, IEEE 802.11 based or other Wi-Fi, cellular, Bluetooth, Infrared, Ethernet, and the like.

Alternatively, or in addition, one could log transactions, for example, using RFID or another transmission modality described above. Thus, for example, a shipper may send unique signals via RFID, Bluetooth, Wi-Fi, etc. to the device 102 and/or a remote device as an indication that the associated object 100 in the form of a package has reached a transshipment and/or final shipment location. The signal and/or an indication that the signal has been received may, for example, be stored in the memory of the device 102. The processor (whether local or remote) may then be programmed to develop an indication of, for example, whether the package containing a perishable item was exposed to a temperature higher than a safety limit for longer than a particular duration during shipment. This enables a shipper to determine whether acceptable shipment delays and/or shipping conditions have been exceeded.

The magnitude of one or more sensed parameters could be stored, whether at a single time, at multiple discrete times, or continuously over one or more periods of time. Alternatively, or in addition, a different condition may be detected, as indicated by one or more other parameters exceeding or falling below a threshold, and the condition may be detected a single time or multiple times. In the latter case, the detection may occur at discrete times or may occur continuously over one or more periods of time.

Figure 2:
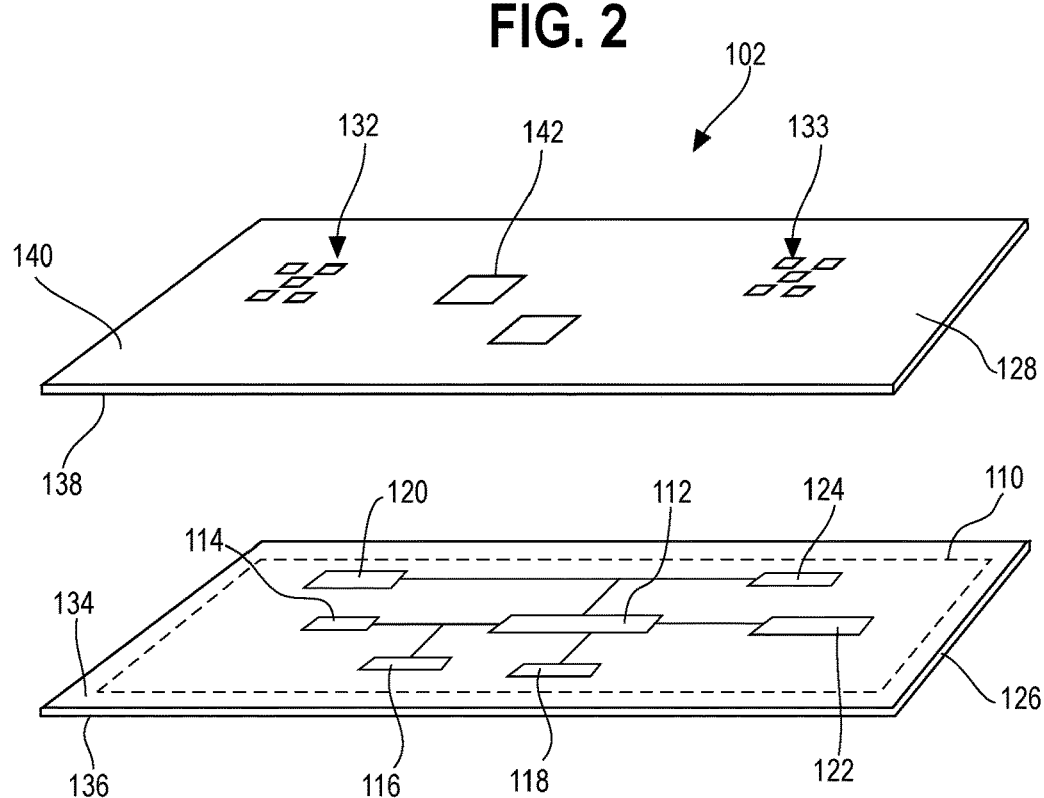
FIG. 2 is an isometric exploded view of the monitoring device of FIG. 1A or 1B.
Figure 5:
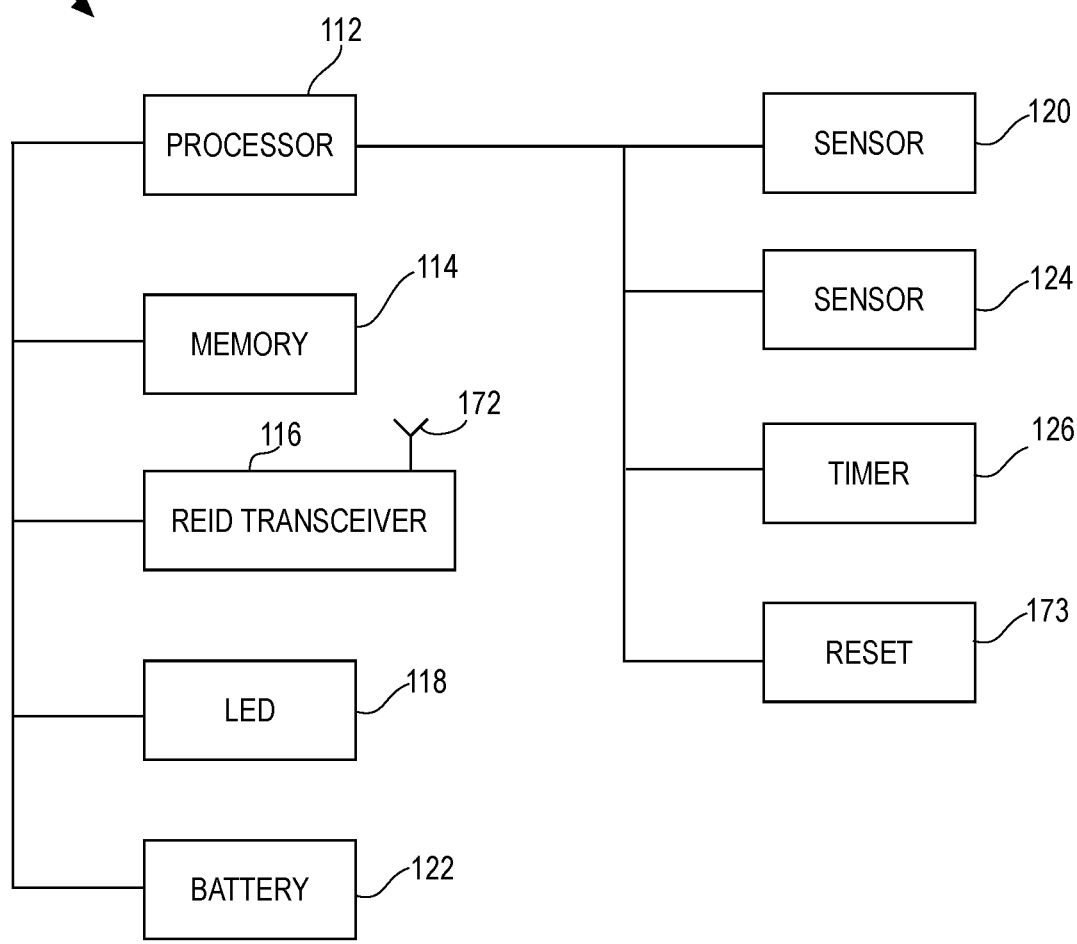
FIG. 5 is a block diagram of the electronic circuit of FIG. 2.

Referring to FIGS. 2 and 5, in one embodiment, the device 102 comprises an electrical circuit 110 that includes a processor 112, an associated memory 114, an RFID transceiver 116, an LED 118, a first sensor 120, a battery 122, and a second sensor 124. The electrical circuit 110 is disposed on a first carrier or substrate 126. Some or all of the components of the electrical circuit 110 may be printed or otherwise formed on the substrate 126 using one or more conductive and/or semiconductive materials. The printing process may employ one or more of lithographic, flexographic, offset, photographic, xerographic, letterpress, gravure, ink jet (drop-on-demand and/or continuous), bubble jet, vapor deposition, screen printing, and/or foil transfer technologies or any other suitable process(es).

In one embodiment, the monitoring device 102 further comprises a second carrier or substrate 128. The second carrier 128 is disposed over the first carrier 126 and includes a first and second plurality of holes 132, 133 respectively that expose the sensors 120, 124 to ambient air. If desired, one or both of the pluralities of holes 132, 133 may be replaced by a relatively larger window or windows or may be replaced by one or more permeable membranes. The first substrate 126 has an inner surface 134 and an outer surface 136, and the second substrate 128 has an inner surface 138 and an outer surface 140. An electrical circuit 110 is disposed between the inner surface 134 of the first substrate 126 and the inner surface 138 of the second substrate 128. At least a portion of the inner surface 134 of the first substrate 126 and a portion of the inner surface 138 of the second substrate 128 are affixed to one another to protect the electronic circuit 110 disposed therebetween.

Each of the carriers or substrates 126, 128 may comprise single or multiple sections or portions made of coated or uncoated paper, cardboard, and/or cardstock, a thermoplastic or other polymer (flexible or otherwise), a film, a textile, a woven material, a gel, an epoxy, fiberglass, a dielectric material, or any other suitable material or any combination(s) thereof. The substrates 126 and 128 may comprise identical or different materials.

In some embodiments, one of outer surfaces 136 or 140 may be adhesively attached or otherwise secured to a surface (outer surface 104 or inner surface 106, FIG. 1) of the object 100. In other embodiments, one of the outer surfaces 136 or 140 may be adhesively secured to an interior surface (not shown) inside of an object (e.g., a vehicle) in a location that is visible to a driver and/or other occupant(s) or is out of view of the occupant(s). In still other embodiments, the monitoring device 102 may be deposited in the interior (not shown) of a room, or affixed to the exterior surface of an object such as a backpack, a package, or other portable objects.

In one specific embodiment seen in FIG. 2, the electronic circuit 110 may comprise conductive traces deposited such as by printing or otherwise formed on the inner surface 134. One or more electronic components may be adhesively secured to the inner surface 134 and/or the conductive traces such that each electronic component is aligned with and electrically coupled to the one or more conductive traces. In some embodiments, the conductive traces may be formed by applying a layer of conductive material on the inner surface 134 and selectively removing, for example, portions of the conductive material by etching or other removal process(es), thereby leaving the conductive traces. In other embodiments, the conductive traces may be formed by selectively depositing the conductive material on the inner surface 134 using, for example, ink jet printing. In still other embodiments, the conductive traces may be formed by printing the conductive material on the inner surface 134 using other printing techniques (e.g., screen, lithographic offset, gravure, flexography, and the like). The electrical circuit 110 may comprise solder flows and/or conductive adhesives to obtain at least portions of conductive traces, and/or to couple electronic components of the electronic circuit 110 to the conductive traces of the electronic circuit 110. Other ways of forming the conductive traces on the inner surface 134 will be apparent to those having ordinary skill in the art.

In another embodiment, the electronic circuit 110 may comprise a pre-formed circuit on a substrate, for example, a substrate similar or identical to one or both of the first and second substrates 126, 128, a printed circuit board, or the like and such substrate may be deposited between the inner surfaces 134, 138 or the pre-formed circuit may be disposed on either or both of the surfaces 134, 138 or any other surface(s). In some cases, conductive traces and/or some components of the circuit 110 may be deposited on one or both of the surfaces 134 and 138, and remaining conductive traces) and/or component(s) of the circuit 110 may be disposed on a further substrate. The further substrate may then be affixed to one or both of the surfaces 134 and 138 and the substrates 126, 128 may be assembled together as noted above with the further substrate sandwiched therebetween such that the components on the further substrate are electrically coupled with the circuit traces on the one or more surfaces 134 and 138.

In one embodiment, coupling two or more conductive traces together may generate a reset signal. For example, portions of the conductive traces may be exposed through the aperture, and an object, such as a switch or a button 142, may be used to short such exposed portions. The object may comprise a push button, a soft button, a low excursion button, or the like. Alternatively, ends of the traces may be manually deflectable into contact with one another.

Figure 3A:
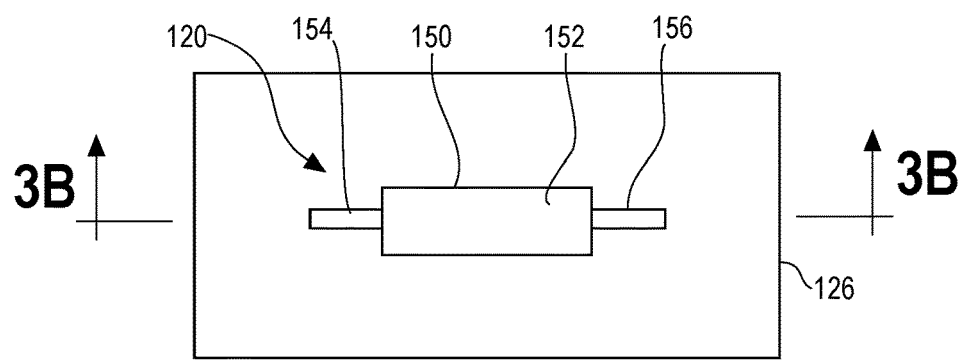
FIG. 3A is a plan view of the first sensor of FIG. 2.
Figure 3B:
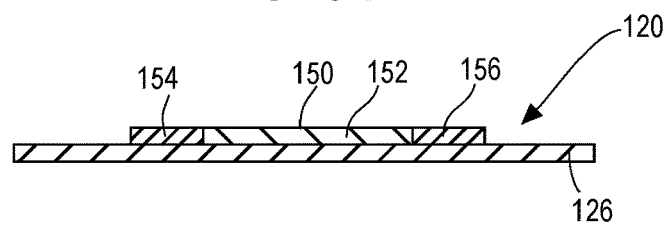
FIG. 3B is a sectional view taken generally along the lines 3B-3B of FIG. 3A.

Referring to FIG. 3A and FIG. 3B, in one embodiment the first sensor 120 is a monolayer structure 150 that comprises a conductive or semiconductive material, for example, a polymer 152, a first terminal 154 and a second terminal 156. The electrical resistance across the conductive polymer 152 is measured to obtain an indication of an amount of airborne alkali materials in the ambient surroundings of the monitoring device 102.

Specifically, in one embodiment, the first sensor comprises a body of semiconducting polymer, such as polyaniline. As alkali molecules in the ambient surroundings contact and bind to the conductive polymer (and are thereby adsorbed on the surface of the polymer), the resistance across the conductive polymer increases. The polyaniline may optionally be doped with other compounds to make the polymer reactive to other materials. Other suitable conductive or semiconductive polymers include polycarbazole, polypyrrole, polythiophene, polyacetylene, and compounds containing such polymers, and combination(s) thereof.

The semiconductive polymer is applied to the carrier substrate by a printing means such as one or more of ink jet or bubble jet (either being of the thermal or piezoelectric type), in which case the polymer comprises a jettable composition comprising: a polymer, one or more solvents, a pH modifier, and one or more surfactants. Alternatively or additionally, the polymer may be applied to the carrier by other processes, in which case the polymer may comprise a compound suitable for use in such process(es).

Figure 4A:
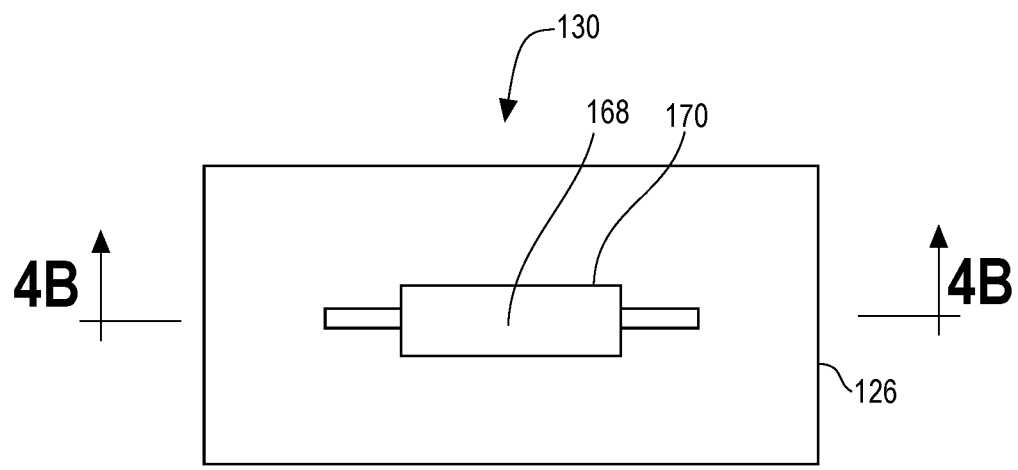
FIG. 4A is a plan view of the second sensor of FIG. 2.
Figure 4B:
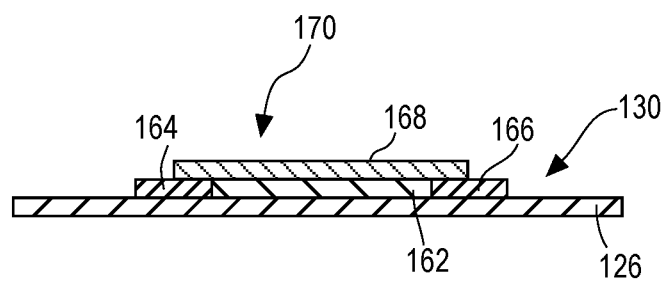
FIG. 4B is a sectional view taken generally along the lines 4B-4B of FIG. 4A.

Referring to FIG. 4A and FIG. 4B, the second sensor 124 includes a second conductive polymer 162, a third terminal 164, a fourth terminal 166, and a third polymer 168. The second conductive polymer 162 and third polymer 168 form a bilayer structure 170.

The third polymer 168 is applied on top of the second conductive polymer 162 and provides a barrier to certain molecules, such as nicotine, while allowing other molecules, such as alcohols and ammonia, to pass through and contact the second conductive polymer 162. The third polymer 168 is most preferably a selectively permeable material such as polyvinyl alcohol (PVA). The second sensor 124 allows the processor 112 to determine how much of the alkali materials sensed by the first sensor are alcohols or ammonia (and not nicotine).

Specifically, if the first and second sensors are exposed to ammonia, both will exhibit an increase in resistance. The increase in resistance due to the adsorption of these materials is, under some condition, reversible. If the first and second sensors are exposed to nicotine and not to other alkali materials, only the first sensor, lacking the third polymer to block the flow of nicotine to the conductive polymer, will exhibit an increase in resistance. Using multiple sensors that detect different groups of molecules allows for determination of the concentration of a chemical that is a member of a group of chemicals that can be sensed by one or more of the sensors, but not all of the sensors.

On a general level, one could provide two or more sensors, e.g., 120 and 124, adapted to detect the presence of at least two elements and/or compounds or classes of compounds. The processor 112 may be responsive to the outputs of the sensors to develop an indication of the presence of an element and/or a compound. Each of the sensors 120, 124 may develop a binary output indicating the presence or absence of an element/compound, or one or both sensors may develop an analog or binary signal representing a magnitude or other parameter of a characteristic of the element/compound. The processor 112 may be responsive to the outputs of sensors 120, 124 individually or may combine the sensor outputs in any suitable way to obtain the indication. Thus, for example, the processor 112 may compare the magnitudes of the sensor outputs, undertake a boolean or arithmetic or other mathematical combination of the output magnitudes of the sensors or otherwise take the outputs of the sensors into account to develop the indication.

In the illustrated embodiment, the resistance of each sensor 120, 124 is detected by causing the processor 112 to develop a voltage of known magnitude(s) across each sensor 120, 124 and detect the magnitude of the resulting current magnitude(s) flowing through each sensor 120, 124. Alternatively, a current of known magnitude(s) may be delivered to each sensor 120, 124 and the voltage magnitudes(s) developed thereacross may be detected. In any event, if the resistance of the first sensor 120 exceeds a first magnitude, then it has been determined that airborne alkali materials are present above a threshold concentration in the environment of the object. Once this condition is detected, the processor 112 polls the second sensor 124 to determine whether the resistance of the second sensor 124 has increased above a second magnitude. If the resistance of the second sensor 124 has increased above the second magnitude, the processor 112 determines that the monitoring device 102 has been exposed to alcohol or some other alkali material. If the resistance of the second sensor 124 has not increased above the second magnitude, then the processor determines that the monitoring device 102 has been exposed to nicotine.

Further sensors may be used to detect temperature and/or moisture. A carbon based moisture detector to facilitate detection of water-based ammonia or low molecular weight amine compositions (such as window cleaning products, floor wax products, waterborne paints and the like) and a temperature sensor to allow the processor to compensate for the effects of temperature in the detectors. These measurements may be used separately or in combination to correct/compensate for effects of temperature and moisture on the monolayer and multilayer sensors 120, 124.

Configuration parameters may be established and stored in the memory 114 including baseline data for nicotine levels in the ambient environment. In one embodiment, a user can press a button while the monitoring device is running to set a baseline level. In another embodiment, baseline data can be received via an RFID transceiver or other communication means and may be stored in the memory 114 of the monitoring device 102. The processor 112 may develop an indication of nicotine exposure when the baseline level is exceeded by a predetermined amount. Optionally, the indication of nicotine exposure may be developed when the baseline level of nicotine is exceeded over a particular continuous period of time of when the baseline level is exceeded for a cumulative discontinuous time.

Referring to FIG. 5, the RFID transceiver 116 is coupled to one or more antennas 172. The electronic circuit 110 also includes a reset signal generator 173 coupled to the processor 112. Measurements of the resistance across each of the two sensors may be processed using known signal processing and filtering operations to determine the amount of nicotine detected by the monitoring device 102. Such measurements are stored in the memory 114. The processor may also digitally filter the signals from the various detectors to determine the rate of nicotine/ammonia uptake versus time.

In one embodiment, the processor 112, the memory 114, the RFID transceiver 116, and the sensors 120, 124 are coupled with one another to transfer data therebetween. For example, in one embodiment, the processor 112, the memory 114, the RFID transceiver 116, and the sensors 120, 124 may be coupled using serial or parallel communication protocols. Such communication protocols may include for example an architecture in accordance with the Inter-Integrated Circuit (I2C) specification, a Serial Peripheral Interface (SPI) developed by Motorola, Inc. of Schaumburg, Ill., or the like. Other ways of coupling such electronic components will be apparent to those having ordinary skill in the art.

In an embodiment, the sensors 120, 124 and the optional further sensor (not shown) may include a nicotine sensor, an alkaline material sensor, a monolayer sensor, a bilayer sensor, a fluid sensor, a carbon monoxide sensor, an accelerometer, a tilt-sensor (which may or may not comprise the noted accelerometer), a temperature sensor, a humidity sensor, and the like. In some cases, a further sensor may be able to detect multiple conditions. For example, a sensor such as the HTU21D(F) sensor manufactured by Measurement Specialties of Hampton, Virginia may be used to sense both humidity and temperature.

Referring to FIGS. 2 and 5, in one embodiment, configuration parameters are supplied to the monitoring device 102 by any suitable device(s), such as a separate processor and/or transceiver, and stored in a predetermined segment of the memory 114 reserved for configuration parameters, as described below. Such configuration parameters specify what ambient/environmental conditions are to be monitored by the monitoring device 102 and the acceptable ranges and/or thresholds for such conditions. If the monitoring device 102 is subjected to one or more ambient/environmental conditions that is outside of the acceptable range(s) therefor, the processor 112 records one or more entries that include, for example, time(s) when such ambient/environmental condition occurred, and the magnitude(s) of such ambient/environmental condition in the portion of the memory 114 reserved for monitoring data. Such entry or entries may include additional information as should be apparent to those of ordinary skill in the art.

In some embodiments, the monitoring data recorded by the processor 112 includes a value that indicates an amount of elapsed time between when a reset signal was generated by the reset signal generator 173 or otherwise and when an ambient/environmental condition outside the acceptable range(s) was sensed. The amount of elapsed time may be measured in milliseconds, seconds, ticks of a clock device, or some other time measure. In some embodiments, an operator may record the actual time of day when the reset signal was generated on an external device, for example. The calendar time when the force or environmental condition was sensed may be derived by adding the amount of elapsed time represented by the value recorded in the monitoring data to the calendar time recorded when the reset signal was generated.

For example, if the sensors 120, 124 include a first chemical sensor and a second chemical sensor, the configuration parameters may specify that monitoring device 102 should record an entry in the portion of the memory 114 if the first sensor detects a first chemical in a concentration above or below a first configuration value and a separate entry if the second sensor determines that the object 100 is exposed to a second chemical in a concentration above or below a second configuration value. Such configuration parameters may be selected, for example, in accordance with the contents of the object 100 to which the monitoring device 102 is affixed.

The monitoring device 102 may be affixed to the object 100 before or after the configuration parameters are stored in the portion of the memory 114 reserved for configuration parameters. In a specific embodiment, the processor 112 includes or communicates with registers that are loaded with configuration parameters.

Figure 6:
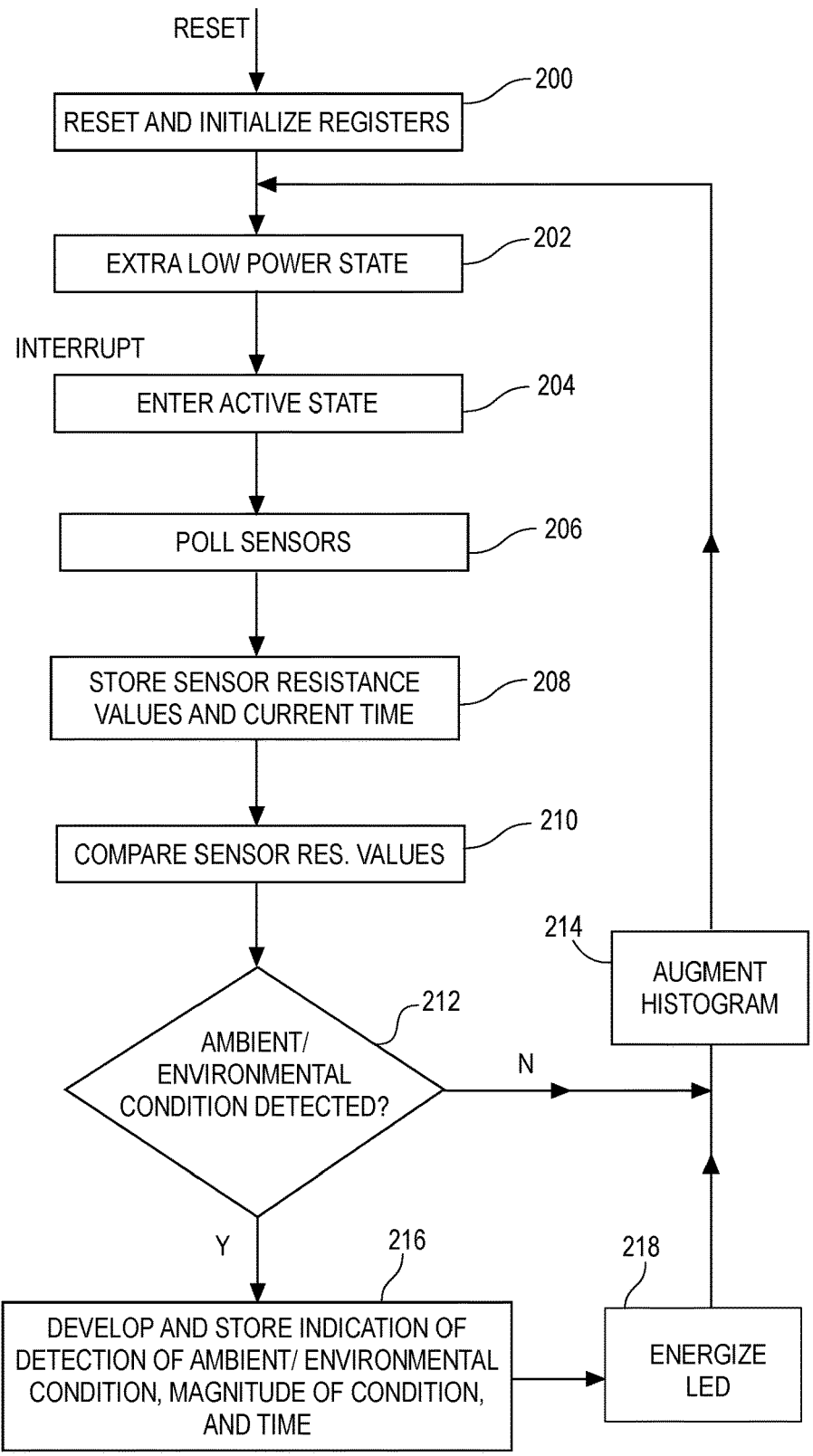
FIG. 6 is a flowchart illustrating operation of the processor of FIG. 5 according to a first embodiment.

Referring to FIG. 6, in a specific embodiment, the first sensor comprises a conductive polymer monolayer structure configured to detect when the object is subjected to at least a first magnitude of a first condition. The second sensor comprises a second conductive polymer and third polymer that form a bilayer structure configured to detect when the object is subjected to a first magnitude of a second condition. The configuration parameters specify a first configuration parameter and a second configuration parameter. The configuration parameters include a second magnitude of the first condition, and a second magnitude of the second condition. A comparison is made of the first magnitudes and the second magnitudes and used to determine the level of nicotine exposure the object has encountered.

Referring to FIG. 6, after the monitoring device 102 is affixed to the object 100 (e.g., a vehicle), the reset signal generator 173 is actuated by depressing the switch 142 to provide a reset signal to the processor 112. In response to such signal, a block 200 causes registers in the memory 114 to be reset and loaded with initial configuration parameter values. A block 202 then causes the processor 112 to assume an inactive state during which the processor 112 undertakes only minimal activity and thus consumes little power. Upon generation of an interrupt by one or both of the sensors 120, 124 or by a timer, such as the timer 126, the processor 112 transitions to an active state, reads the configuration parameter values from the memory 114, and configures the processor 112 (and, optionally, the sensors 120, 124) in accordance with such configuration parameters.

In some embodiments, the sensors 120 and/or 124 may be purely passive and incapable of actively developing an interrupt, such as the sensors 120, 124 described above. Alternatively, one or both of the sensors 120, 124 (either alone or in combination with other element(s)) may be of the active type capable of developing an interrupt signal when a parameter magnitude exceeds or drops below a certain magnitude. In the case where one or more sensors 120, 124 are of the active type, the processor 112 may directly communicate such parameter magnitude(s) to the selected sensor(s) 120, 124, or the processor 112 may write such parameters to a particular memory location that may be accessed by the sensor(s) 120, 124. In such embodiments, the active sensor 120 and/or 124 may load the parameter magnitude(s) from the memory location when upon receipt of a signal from the processor 112 or the reset signal generator 173. If the selected sensor 120 and/or 124 is programmable to generate an interrupt upon detection of a particular condition, such as a sensed condition exceeds or falls below a particular parameter magnitude, the processor 112 so programs the selected sensor 120. If the selected sensor 120 and/or 124 is passive and cannot generate an interrupt upon detection of the particular condition, the processor 112 stores the particular parameter magnitude(s) together with a list of sensors 120, 124 to be polled periodically in the memory 114. The following description assumes that the sensors 120, 124 are purely passive, and are periodically polled as described hereinafter.

For each sensor 120, 124 that has to be polled periodically, the processor 112 sets an associated timer 126 that generates a periodic interrupt. The period of each interrupt signal may be based on the sensors 120, 124 to be polled or the particular condition to be detected. Different predetermined periods of time may be associated with different conditions to be detected. In some embodiments, such predetermined period may be specified by the configuration parameters. Alternatively or in addition, a single timer 126 may periodically generate an interrupt signal that causes both of the sensors 120, 124 to be polled at the same time. The following description assumes that a single timer 126 develops a periodic or spa periodic interrupt signal that causes the processor 112 to check both sensors 120, 124.

In the illustrated embodiment, after configuring the sensors 120, 124 and/or setting the timer 126, the processor 112 transitions to a sleep state 202 in which the processor 112 is inactive when the processor 112 is in the inactive or the sleep state, the processor 112 is in a reduced power state to minimize power drain. The processor 112 is minimally active to track time, monitor signals from the timer or an interrupt source coupled to an input the processor 112, and/or execute minimal program instructions. Upon generation of an interrupt signal by the timer 126, the processor 112 enters an active state 204.

Once power up is complete, a block 206 checks the first and second sensors 120, 124 and from each such sensors 120, 124 obtains a measurement of the condition detected by each sensor 120, 124 by determining the resistances thereof. A block 208 stores the sensor resistances and the current time and stores such values in the memory 114. A block 210 compares the most recent resistance values stored in the memory 114. Alternatively, the resistance value may first be converted to gaseous or particulate concentration magnitudes and those values may be compared by the block 210. In either event, such comparison may be effected automatically, boolean, or otherwise. In the illustrated embodiment, the reading from the sensor 124 is subtracted from the reading from the sensor 120. The block 212 then checks to determine whether the result of such comparison exceed a comparison threshold. If the result exceeds the comparison threshold, then the block 212 has determined that the ambient/environmental condition has not been detected, and control passes to an optional block 214 which updates a histogram stored in the memory 114 with time and comparison values, provided that the histogram has not already been updated by another block, such as the block 208. Control then returns to the low power state block 202.

If the block 212 determines that the comparison result obtained by the block 210 exceeds the comparison threshold, control passes to a block 216, which develops and stores in the memory 114 an indication that the ambient/environmental condition has been detected together with the current time. In addition, the bock 216 may store in the memory 114 an indication of the magnitude of the ambient/environmental condition. This indication may simply be the result of the comparison effected by the block 210. Thereafter, control passes to an optional block 218, which energizes an optional indicator, such as the LED 118, and control then passes to the blocks 214 and 202.

If desired, the block may poll one or more other sensors, such as the temperature sensor and/or a moisture sensor.

In this case, the processor 112 stores such measurements in the portion of the memory 114 reserved for monitoring data, and in some embodiments, further stores a timestamp of when such measurement(s) were acquired.

In another embodiment, the processor responds to a reading of at least a particular magnitude from a first sensor by polling the second sensor, as opposed to polling both sensors substantially simultaneously. The processor reads and analyzes the data from the sensors to determine whether a substance (e.g., nicotine) has been detected for example, as described above.

In some embodiments, the processor 112 may be configured to respond to a reset signal when in the sleep state. In such embodiments, receipt of the reset signal causes the processor 112 to transition to a stop monitoring state, in which the processor 112 instructs the timer 126 to disable any scheduled wake-up signals. Alternatively, the processor 112 may be programmed to ignore any wake-up signals and interrupts. In such embodiment, the processor 112 may record in the portion of the memory 114 reserved for monitoring data that the reset signal was received thereby, and in some cases, a timestamp when the reset signal was received. Thereafter, the processor 112 transitions to the inactive state until a further reset signal is received.

Instructions executed by the processor 112 to undertake the actions described above may be stored in a non-transient memory internal to the processor 112 or in a predetermined segment of the memory 114 reserved for program instructions. Such memory may also include default or predetermined configuration parameters that may be used if additional or different configuration parameters are not supplied to the monitoring device 102. The monitoring device 102 may comprise a programmable element, discrete components, firmware, or a combination thereof and the functions undertaken by the processor 112 may be implemented by programming and/or by hardware and/or firmware as desired. In some embodiments, the processor 112, and memory in which to store instructions executed by such processor 112 to operate the monitoring device 102, may be provided by an individual component such as an application-specific integrated circuit (ASIC), a field-programmable gate array (FPGA), a discrete logic device, a state machine, and the like.

In an exemplary embodiment of the electronic circuit 110 of the monitoring device 102, the processor 112, the memory 114, and the RFID transceiver 116 are coupled by a conductive trace to an output of a clock signal source. A data input and output pin of each of the components 112, 114, and 116 are coupled to a common conductive trace. In accordance with the I2C protocol, a clock signal supplied by the clock signal source on the conductive trace provides a timing signal to gate the data transmitted or received on the conductive trace.

The electronic circuit 110 optionally includes a humidity and temperature sensor and an accelerometer and tilt sensor. In this specific embodiment the humidity and temperature sensor does not generate interrupt signals in response to detection of particular humidity levels and/or temperatures. Therefore, as described above, the processor 112 polls the humidity and temperature sensor periodically to determine if such environmental conditions exceed the thresholds supplied for such conditions in the configuration parameters. A carbon based moisture detector facilitates detection of solvent-based ammonia and a temperature sensor to allow the processor to compensate for the effects of temperature in the detectors.

The first sensor and second sensor may be configured with particular thresholds, and in the illustrated embodiment generates an interrupt on an output thereof if such threshold is exceeded. The outputs of the first sensor and second sensor are coupled by a conductive trace to an input pin of the processor 112. When the processor 112 is in the sleep state, an interrupt signal on the input pin causes a transition of the processor 112 from the sleep state to the read sensor data state to store data from the sensor in the portion of the memory 114 reserved for monitoring data. As described above, the processor 112 may also store a timestamp of when the interrupt signal was generated in the portion of the memory 114, in addition to the data from the sensor.

The reset signal generator 173 is coupled to an input pin of the processor 112 by a conductive trace. In some embodiments, actuation of the reset signal generator 173 causes a predetermined high state reset voltage to be developed on the conductive trace, and in response thereto, the processor 112 responds to such reset signal as described above. In other embodiments, actuation of the reset signal generator 173 causes a predetermined low state reset voltage to be developed on the conductive trace, in turn to cause the processor 112 to respond as described above. Actuation of a reset actuator may cause the reset signal generator 173 to generate the reset signal. In some embodiments, the reset actuator may include a switch that is actuated, a pair of conductive traces are coupled, a pair of conductive traces are decoupled, and/or a button.

In some embodiments, the electronic circuit 110 includes a data pad to which an external device may be connected to monitor data and/or signals transmitted over the conductive trace, for example, for diagnostic purposes.

The electronic circuit 110 may also include pull-up resistors to permit interrupts and data to be written and read and a capacitor that facilitates proper operation of the sensor. In addition, a battery 122, for example, a thin-film battery, provides voltage to a power rail from which the components of the electronic circuit 110 may draw power, and a common ground.

In some embodiments, the electronic circuit 110 may comprise a light emitting diode 118 that is briefly illuminated when the processor 112 is reset. In some embodiments, the processor 112 may illuminate such light emitting diode 118 when the processor 112 receives the reset signal. In other embodiments, the reset signal generator 173 may illuminate such light emitting diode when an ambient/environmental condition is detected. The electronic circuit 110 may include other types of components such another type of light emitter, a sound generator, a vibration generator, and the like that may be actuated instead of or in addition to the light emitting diode to indicate when the processor 112 is reset.

In some embodiments, configuration parameters may be supplied to monitoring device 102 by transmitting such parameters to the RFID transceiver 116 via one or more RFID antennas 172. Upon receipt of such transmission, the RFID transceiver 116 writes the received configuration parameters in the portion of the memory 114 reserved for configuration parameters. In other embodiments, the monitoring device 102 includes uncovered or covered apertures through which conductive traces may be shorted or opened, to cause the configuration parameters to be supplied to the processor 112 and the memory 114. In some embodiments, such apertures may be covered with removable tabs, and removal of one or more such tabs decouples conductive traces associated with the tab, and thereby selects the configuration parameters supplied to the processor 112 and the memory 114. Configuration parameters may be supplied to some embodiments of the monitoring device 102 using a combination of transmission to the RFID transceiver(s) 116, pressing of one or more buttons, and shorting or opening of one or more pairs of conductive traces.

In still further embodiments, the processor 112 enters a store configuration parameters state from the inactive state when a digital value is received from an analog-to-digital converter. In such state, the processor 112 reads the digital value, and reads from the memory 114 or an internal memory (not shown) predetermined configuration parameters associated with such digital value, and stores such predetermined configuration parameters in the portion of the memory 114 reserved for configuration parameters. Thereafter, the processor 112 returns to the inactive state. The transitions into the configuration state by the processor 112 in response to receipt of a reset signal and the sleep state from the configuration state are as described above. Similarly, the transitions by the processor 112 into the poll sensor, read sensor data, and stop monitoring states in response to a wake up signal, a sensor interrupt, and a further reset signal are as described above.

At any time, an RFID reader may be used to direct the RFID transceiver 116 to read any entries stored in the portion of the memory 114 reserved for monitoring data. In response, the RFID transceiver 116 reads and transmits such entries to the RFID reader so that such entries may be inspected to determine if the monitoring device 102, and therefore the object 100 to which such device is affixed, was subjected to conditions outside of those specified by the configuration parameters previously supplied to the monitoring device 102.

A monitoring device for detecting that an object has been subjected to a particular condition in accordance with the above may comprise a carrier disposed on the object, a processor disposed on the carrier, a first sensor and second sensor disposed on the carrier, and a configuration circuit. The sensors may be adapted to detect when the object is subjected to at least a first magnitude of the first and second conditions. The configuration circuit may specify configuration parameters, wherein the configuration parameters includes second magnitudes of the first and second conditions. The processor may remain in an inactive state if the object is subjected to a magnitude of the first condition less than the second configuration parameter, the sensor may generate a signal in response to detection of the object being subjected to a magnitude of the first condition, and in response to the signal the processor may enter an active state to develop an indication of a magnitude of the second condition, wherein the magnitude is less than the second configuration parameter. For example, in the case of dual sensor for sensing nicotine comprising a first sensor for sensing alkaline materials, and a second sensor sensing ammonia and alcohol, if the amount of alkaline material sensed by a first sensor does not exceed a first magnitude, the second sensor would not be polled. If the amount of alkaline material sensed by the first sensor does exceed a first magnitude, the second sensor would be polled.

The processor of such a monitoring device processor may return to the inactive state after the indication has been developed, and the processor may remain in the inactive state until the sensor detects that the object is subjected to a fourth magnitude of the particular condition, wherein the fourth magnitude is greater the third magnitude.

Such monitoring device may comprise a further sensor that may be configured to sense a further condition to which the object may be subjected, and the processor periodically may poll the further sensor to determine if the object has been subjected to the further condition.

The carrier of the monitoring device may comprise a first surface and a second surface opposite the first surface, the processor and the sensor may be disposed on the first surface, and the second surface may be affixed to the object. The monitoring device may further comprise conductive traces coupled to the processor and the sensor, wherein the conductive traces may be printed on the first surface using one or more of inkjet printing, screen printing, lithographic printing, intaglio printing, gravure printing and flexographic printing.

The configuration circuit of the monitoring device may include an RFID transceiver, and the configuration parameter may be transmitted to the RFID transceiver. The configuration circuit may include two conductive traces associated with the configuration parameter, wherein coupling the two conductive traces specifies the second magnitude. The monitoring device may include a further carrier, wherein the two conductive traces may be disposed between the carrier and the further carrier, and the further carrier may include an aperture through which the two conductive traces may be coupled. The further carrier may include a further aperture and two further conductive traces that may be coupled through the further aperture, wherein coupling the two further conductive traces may specify further configuration parameters. In the illustrated embodiment, the further carrier covers at least a portion of the processor, the first polymer sensor, and the second polymer sensor.

The configuration circuit of the monitoring device may include two conductive traces that may be decoupled, and decoupling the two conductive traces may specify the second magnitude. The monitoring device may include a further carrier having a button 160, wherein pressing the button decouples the two conductive traces. In addition, the further carrier may include a further button, wherein pressing the further button specifies a further configuration parameter. The button(s) may include a surface having a conductive portion and the conductive portion couples the two conductive traces. Pressing a button 160 of the monitoring device may generate a reset signal to the processor.

In some cases, the processor of the monitoring device may configure the sensors in accordance with the configuration parameter.

The monitoring device may also include a reset signal generator to generate a reset signal that actuates the monitoring device. The reset signal generator may include two conductive traces that may be coupled, wherein the reset signal is generated when the two conductive traces are coupled. Alternately, the reset signal generator may include two conductive traces that may be decoupled, wherein the reset signal is generated when the two conductive traces are decoupled. Further, pressing a button would allow a user to acknowledge the presence of an ambient/environmental condition.

The carrier of the monitoring device may include a switch, a memory, one or more holes, and one or more buttons, wherein actuation of the switch causes the processor to record the buttons that have been pressed. In response to actuation of the switch, the processor may record in the memory a plurality of configuration parameters determined by the buttons. In some cases, if none of the buttons has been pressed, the processor, in response to actuation of the switch, may record in the memory predefined configuration parameters.

In one embodiment, the first polymer sensor and second polymer sensor of the device may be heated to drive off or vaporize the absorbed material (such as nicotine, alkaline materials, water, etc.). Heating the polymer sensors causes a substantial portion of the absorbed material to be driven off so that the sensor can return to the baseline resistance levels. In one embodiment, the resetting of the sensor by heating can be followed by establishing a new baseline value, for example, by operating the heater to remove only a portion of the absorbed material.

Heating of the polymer sensors may be achieved by passing current through the sensors. This could be accomplished locally via battery power or externally. Alternative sources of heating can include external means for heating such as radiation (UV or infrared light) or convective heat transfer.

INDUSTRIAL APPLICABILITY

It should be apparent that the various embodiments of sensors to monitor conditions, configure the monitoring device 102 and generate the reset signal described hereinabove may be combined into any monitoring device. Other monitoring devices may include various combinations of one or more elements of the embodiments disclosed herein as appropriate in accordance with the intended use of the monitoring device.

The use of the terms "a" and "an" and "the" and similar references in the context of describing the embodiments herein are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Numerous modifications to the present disclosure will be apparent to those skilled in the art in view of the foregoing description. Preferred embodiments of this disclosure are described herein, including the best mode known to the inventors for carrying out the disclosure. It should be understood that the illustrated embodiments are exemplary only, and should not be taken as limiting the scope of the disclosure.

What is claimed is:

1. A monitoring device for detecting a particular condition, comprising:
   a first carrier;
   a processor disposed on the first carrier;
   a first sensor disposed on the first carrier, wherein the first sensor is coupled to the processor and configured to detect when the monitoring device is subjected to at least a first magnitude of a first condition;
   a second sensor disposed on the first carrier, wherein the second sensor is coupled to the processor and configured to detect when the monitoring device is subjected to at least a second magnitude of a second condition;
   a second carrier disposed over at least a portion of one or more of the processor, the first sensor, and the second sensor,
   wherein the processor is configured to generate a signal in response to detection of the first sensor being subjected to at least the first magnitude of the first condition and the second sensor being subjected to less than the second magnitude of the second condition; and
   wherein the second sensor comprises a bilayer construction of a top layer and a bottom layer, the top layer comprising a selectively permeable polymer configured to provide a barrier to certain molecules and allow other molecules to pass through, the bottom layer comprising a conductive polymer.

2. The monitoring device of claim 1, wherein the first sensor comprises polyaniline.

3. The monitoring device of claim 1, wherein the first carrier comprises a first surface and a second surface opposite the first surface, the processor and the sensor are disposed on the first surface, and the second surface is securable to an object.

4. The monitoring device of claim 3, further comprising conductive traces coupled to the processor and the first sensor, wherein the conductive traces are printed on the first surface using one or more of inkjet printing, screen printing, lithographic printing, intaglio printing, gravure printing and flexographic printing.

5. The monitoring device of claim 1, wherein the processor is configured to develop a magnitude of the particular condition from the first magnitude and the second magnitude and generate a second signal if the magnitude of the particular condition is greater than a baseline value.

6. The monitoring device of claim 1, wherein the top layer of the second sensor comprises polyvinyl alcohol.

7. The monitoring device of claim 6, wherein the second carrier includes an aperture through which the two conductive traces may be coupled.

8. The monitoring device of claim 7, wherein the second carrier includes a further aperture and two further conductive traces that may be coupled through the further aperture, wherein coupling the two further conductive traces specifies a configuration parameter.

9. The monitoring device of claim 1, wherein the processor configures the sensors in accordance with a configuration parameter.

10. The monitoring device of claim 1, further including a reset signal generator to generate a reset signal that actuates the monitoring device.

11. The monitoring device of claim 10, wherein the reset signal generator includes two conductive traces that may be coupled, and wherein the reset signal is generated when the two conductive traces are coupled.

12. The monitoring device of claim 1, wherein the processor is connected to a switch and a memory, and wherein actuation of the switch causes the processor to generate a rest signal.

13. The monitoring device of claim 12, wherein in response to actuation of the switch, the processor polls the first sensor and the second sensor.

14. The monitoring device of claim 1, wherein the first sensor comprises an alkaline material sensor, a carbon monoxide sensor, a temperature sensor, a moisture sensor, a monolayer sensor, a bilayer sensor, an accelerometer, a tilt sensor, or a semiconductive polymer.

15. A method of detecting that a device has been subjected to an environmental condition, comprising:
providing a device comprising a first sensor, a second sensor and a processor, wherein the second sensor comprises a bilayer construction of a top layer and a bottom layer, the top layer comprising a selectively permeable polymer configured to provide a barrier to certain molecules and allow other molecules to pass through, the bottom layer comprising a conductive polymer;
detecting when the first sensor is subjected to at least a first magnitude of a first condition by measuring resistance across the first sensor;
detecting when the second sensor is subjected to less than a second magnitude of a second condition by measuring resistance across the second sensor; and
generating a signal in response to detection of the first sensor being subjected to at least the first magnitude of the first condition and the second sensor being subjected to less than the second magnitude of the second condition.

16. The method of claim 15, comprising the further step of heating the first sensor and the second sensor.

17. The method of claim 16, further comprising the steps of specifying a configuration parameter and the step of transmitting the configuration parameter to an RFID transceiver.

18. The method of claim 17, wherein the first sensor comprises polyaniline.

19. The method of claim 18, wherein the second sensor comprises polyvinyl alcohol.

* * * * *